United States Patent
Tsukii et al.

(10) Patent No.: US 8,211,708 B2
(45) Date of Patent: Jul. 3, 2012

(54) OPTICAL MEASURING DEVICE AND METHOD THEREFOR

(75) Inventors: Ken Tsukii, Tokyo (JP); Toru Takahashi, Tokyo (JP); Shinichi Taguchi, Tokyo (JP); Jie Xu, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 73 days.

(21) Appl. No.: 12/610,396

(22) Filed: Nov. 2, 2009

(65) Prior Publication Data

US 2010/0233753 A1 Sep. 16, 2010

(51) Int. Cl.
*G01N 21/59* (2006.01)
*G01N 21/00* (2006.01)
*C12Q 1/02* (2006.01)
*C12Q 1/00* (2006.01)

(52) U.S. Cl. ............ 436/171; 436/164; 435/29; 435/4; 356/442; 356/441; 356/436; 356/432

(58) Field of Classification Search .................. 436/171, 436/164; 435/29, 4; 356/442, 441, 436, 356/432, 422
See application file for complete search history.

(56) References Cited

U.S. PATENT DOCUMENTS

| 5,312,535 | A | 5/1994 | Waska et al. | |
|---|---|---|---|---|
| 2008/0257072 | A1 * | 10/2008 | Takahashi et al. | 73/864.11 |

FOREIGN PATENT DOCUMENTS

| JP | 09-292326 | 11/1997 |
|---|---|---|
| JP | 10-253624 | 9/1998 |
| JP | 2973387 | 9/1999 |
| JP | 2001-517128 | 10/2001 |
| JP | 2002-514757 | 5/2002 |
| JP | 2002-188993 | 7/2002 |
| WO | WO 98/43071 | 10/1998 |
| WO | WO 99/58958 | 11/1999 |
| WO | WO 2005/103642 | * 11/2005 |

OTHER PUBLICATIONS

U.S. Appl. No. 13/092,740, filed Apr. 22, 2011, Tsukii, et al.
U.S. Appl. No. 12/403,772, filed Mar. 13, 2009, Tsukii, et al.
U.S. Appl. No. 13/176,781, filed Jul. 6, 2011, Tsukii, et al.
Office Action issued Feb. 17, 2012 in Japanese Application No. 2007-319704 (with translation), 7 pages.

* cited by examiner

*Primary Examiner* — Christine T Mui
(74) *Attorney, Agent, or Firm* — Oblon, Spivak, McClelland, Maier & Neustadt, L.L.P.

(57) ABSTRACT

The light measurement apparatus of the invention, in which the light is irradiated to the sample dispersed in the liquid flowing through the flow passage, is used for measuring optical information of the sample. The apparatus includes a light source portion 20 for irradiating the irradiating light L to the liquid 11, a light receiving portion 31 to receive the optical information of the sample S including the irradiating light transmitted through the liquid to generate a receiving light signal SG1, under a condition in which the liquid is irradiated by the irradiating light of the light source portion 20 in a state that a relative position of the sample S to the irradiating light varies at constant speed, a measurement portion 120 for measuring variation of the receiving light signal according to the sample.

33 Claims, 12 Drawing Sheets

K-K cross section

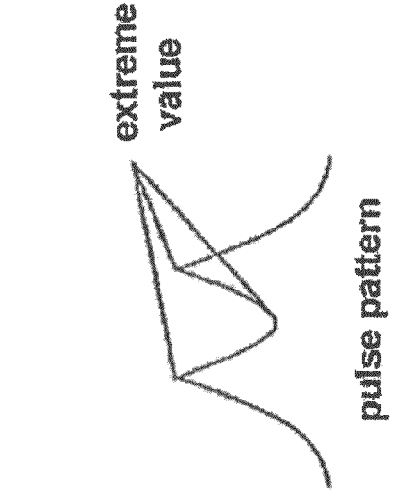
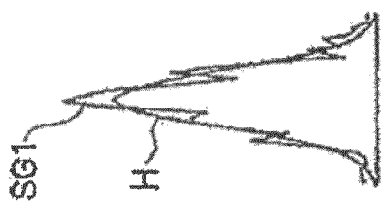
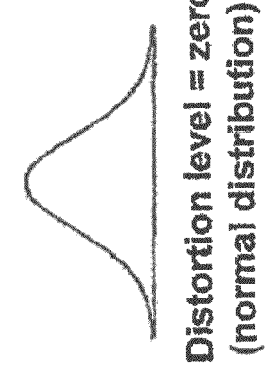
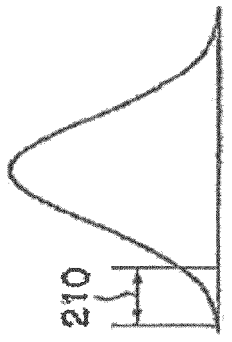
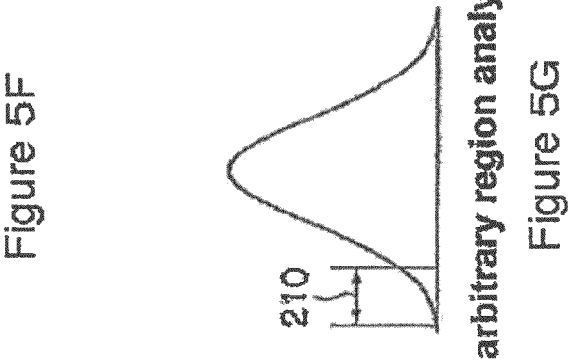
Figure 5A Distortion level = zero (normal distribution)
Figure 5B Distortion level > zero
Figure 5C Steeple level > zero
Figure 5D fitting
Figure 5E peak correction
Figure 5F pulse pattern
Figure 5G arbitrary region analysis Fitting analysis Peak correction

OPTICAL MEASURING DEVICE AND METHOD THEREFOR

BACKGROUND OF THE INVENTION

1. Field of the Invention

The present invention relates to an optical measurement apparatus, in particular to an optical measurement apparatus in which an illuminating light is irradiated to the sample in order to measure optical information of the sample dispersed in the liquid flowing through the flow passage.

2. Description of the Related Art

It is proposed that optical information (fluorescent information) of the sample in the liquid flow is measured in which the liquid with the sample dispersed therein flows in the capillary and the light from the light source is irradiated to the liquid flow (refer to Japanese Patent No. 2973387).

In the measurement apparatus disclosed in the Japanese Patent No. 2973387, a laser light is irradiated through the optical fiber to the sample passing through the capillary. However, it is difficult to precisely measure the shape information of the sample with the use of the transmitted light.

One of the objects of the invention is to provide an optical measurement apparatus, for solving the above described problems, in which the shape information of the sample can be precisely measured.

SUMMARY OF THE INVENTION

In order to solve the above described problems, an optical measurement apparatus for measuring an optical information of a sample by irradiating a single mode light to the sample dispersed in a liquid, which comprises:

a light source portion for irradiating the irradiating light to the liquid;

a light receiving portion to receive the optical information of the sample including the irradiating light transmitted through the liquid to generate a receiving light signal, under a condition in which the liquid is irradiated by the irradiating light of the light source portion in a state that a relative position of the sample to the irradiating light varies at constant speed;

a measurement portion for measuring variation of the receiving light signal according to the sample; and a control portion for analyzing a size, shape and internal structure of the sample from the measured signal.

In the optical measurement apparatus, preferably the sample is dispersed in the fluid flowing through the flow passage.

In the optical measurement apparatus, preferably, the irradiating light for measurement is a non-converging light irradiated through an optical fiber.

In the optical measurement apparatus, preferably, the irradiating light transmitting the liquid is received by the optical fiber.

In the optical measurement apparatus, preferably, the variation of the receiving light according to the sample is the variation of the receiving light signal according to a phenomenon that the relative position of the sample varies at constant speed.

In the optical measurement apparatus, preferably, a variation pattern of the receiving light signal according to the sample is analyzed.

In the optical measurement apparatus, preferably, a maximum value, width, or area of a pulse shape portion in the variation pattern of the receiving light signal is measured.

In the optical measurement apparatus, preferably, the sample size is identified by the maximum value of the pulse shape portion in the variation pattern of the receiving light signal.

In the optical measurement apparatus, preferably, the sample is analyzed by statistical information of an approximate curve of the pulse shape portion in the variation pattern of the receiving light signal.

In the optical measurement apparatus, preferably, the receiving light signal is pattern-analyzed with the pulse shape portion.

In the optical measurement apparatus, preferably, a plurality of peak values is corrected from a variation pattern to analyze a single pulse approximate curve in the receiving light signal.

In the optical measurement apparatus, preferably, an arbitrary region of a variation pattern is information-analyzed to identify a shape of the sample in the receiving light signal.

In the optical measurement apparatus, preferably, the sample is analyzed from the receiving light signal of a plurality of wavelengths.

In the optical measurement apparatus, preferably, a variation pattern is analyzed to identify a kind of the cell in the receiving light signal.

In the optical measurement apparatus, preferably, a specific region in an arbitrary phase of a cell cycle or a region of polyploid nucleus of the sample is recognized.

In the optical measurement apparatus, preferably, a size, shape and/or inner structure of the sample is identified from a plurality of information analyzing a variation pattern of the transmitted light.

In the optical measurement apparatus, preferably, a plurality of light receiving portions receiving the transmitted light is included.

In the optical measurement apparatus, preferably, fluorescent information of the sample and a receiving light signal of a side scattered light In the optical measurement apparatus, preferably, an arbitrary sample is dispensed according to a result of identification.

A light measurement method in which a single mode light is irradiated to a sample dispersed in a liquid to measure optical information including a size, shape and inner structure of the sample, comprising:

irradiating the irradiating light to the liquid from a light source portion;

irradiating the irradiating light from the light source portion to the liquid under a condition in which a relative position of the sample to the irradiating light varies at constant speed;

receiving the optical information of the sample including a measuring light transmitting the liquid to generate receiving light signal; and measuring variation of the receiving light signal of the sample by a measuring portion.

A light measurement method in which a irradiating light is irradiated to a cell in a liquid and a transmitted light transmitting the liquid and the cell is received to measure optical information of the cell, comprising:

irradiating the irradiating light to the cell from a light source portion;

irradiating the irradiating light from the light source portion to the liquid under a condition in which a relative position of the sample to the irradiating light varies at constant speed; and measuring variation of intensity of the transmitted light over time when the transmitted light is received to generate receiving light signal.

In the light measurement method, preferably, attenuation and amplification of the intensity of the transmitted light can be measured.

In the light measurement method, preferably, the intensity of the transmitted light varies depending on cell species or number of cell nucleus to have a wave profile including at least two attenuated wave profile portions.

In the light measurement method, preferably, the intensity of the transmitted light varies depending on cell species or number of cell nucleus to have a wave profile including a repetition of an attenuated wave profile portion and an amplified wave profile portion.

In the light measurement method, preferably, the intensity of the transmitted light varies over time depending on cell attribution and property expressed by number of cell nucleus and size of cell nucleus.

A light measurement method in which a irradiating light is irradiated to a cell in a liquid and a transmitted light transmitting the liquid and the cell is received to measure optical information of the cell, comprising:

irradiating the irradiating light to the cell from a light source portion;

irradiating the irradiating light from the light source portion to the liquid under a condition in which a relative position of the cell to the irradiating light varies at constant speed to receive the transmitted light by light receiving portion;

approximating wave profile of intensity of the transmitted light varied over time to one or plurality of standard template prepared in advance to be separated in layer; and identifying property of the cell.

In the light measurement method, preferably, a kind of the cell or cancer cell representing different property from same kind of cell is specified by wave profile varied over time, including a repetition of an attenuated wave profile portion and an amplified wave profile portion with the use of intensity of the transmitted light.

In the light measurement method, preferably, A kind of particular cell, B kind of particular cell, or B kind of particular cell in the C kind of particular cell is specified with the use of the intensity of the transmitted light, or abnormal cell in A kind of particular cell is specified as cancer cell.

In the light measurement method, preferably, specific cell including blood cell is specified according to the intensity of the transmitted light.

In the light measurement method, preferably, wavelength of the transmitted light is from 325 nm to 900 nm.

In the light measurement method, preferably, the irradiating light irradiated toward the cell from the light source portion expands from the light source portion toward the light receiving portion.

In the light measurement method, preferably, the light receiving portion comprises a CCD (charge-coupled device) camera, and in either state of that the cell flowing in a narrow flow passage or the cell is stationed in the liquid, the intensity of the receiving light signal and the two dimensional distribution state of the intensity of the receiving light signal can be measured by the stationing or varying of the relative position among the cell, the irradiating portion and the light receiving portion.

In the light measurement method, preferably, varied wave profiles of the intensity of the transmitted light to the cell in a parent population are divided into a plurality of groups, and the cell is distinguished from the parent population and evaluated with a frequency distribution of the respective groups.

In the light measurement method, preferably, wave profile is divided in layer into a plurality kinds from a measurement result of wave profile of the transmitted light obtained by a plurality of cells, and a kind of cell and state of cell is specified according to statistical information of each kind to all.

In the light measurement method, preferably, an amplification of the transmitted light is a variation of the intensity of the transmitted light over time measured by interference phenomenon of the transmitted light caused by attribution and property of the cell including size of the cell, and number and size of the cell nucleus.

In the light measurement method, preferably, an arbitrary sample is sorted from an identification result.

In the light measurement method, preferably, a specified cell is dispensed and selected.

In the light measurement method, preferably, selected cell is cultivated, or a prescribed reagent is added to the selected cell, and the variation over time of the selected cell is evaluated.

BRIEF DESCRIPTION OF THE DRAWING

FIG. 5 shows an example of the receiving light signal SG1 obtained in the light receiving portion of the transmitted light depicted in FIG. 1;

DETAILED DESCRIPTION OF THE INVENTION

Preferable embodiments of the invention are described in detail with reference to the drawings.

Figure 1:
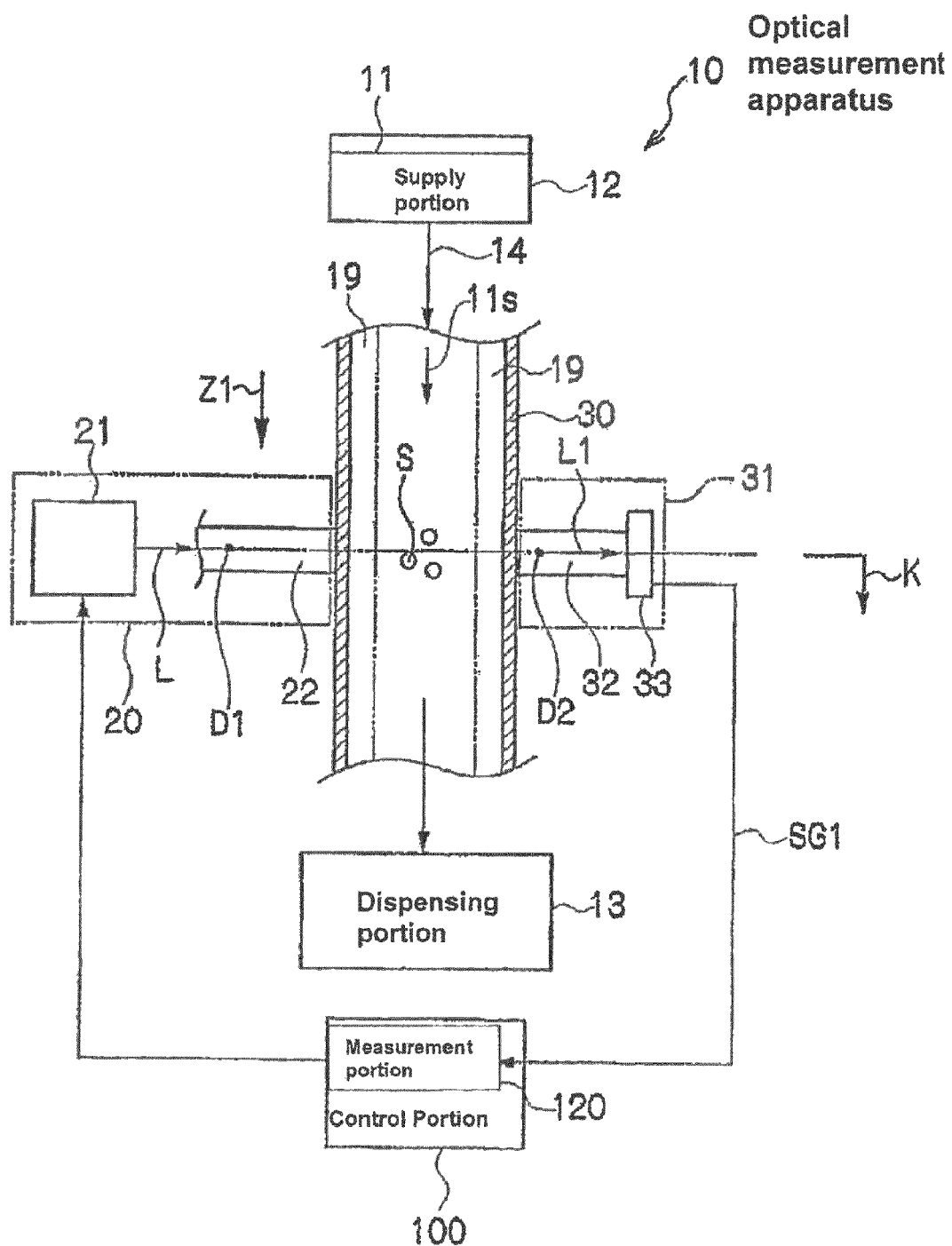
FIG. 1 is a perspective view showing an example of the flow cyte meter including preferable embodiment of the light measurement apparatus of the invention.
Figure 2:
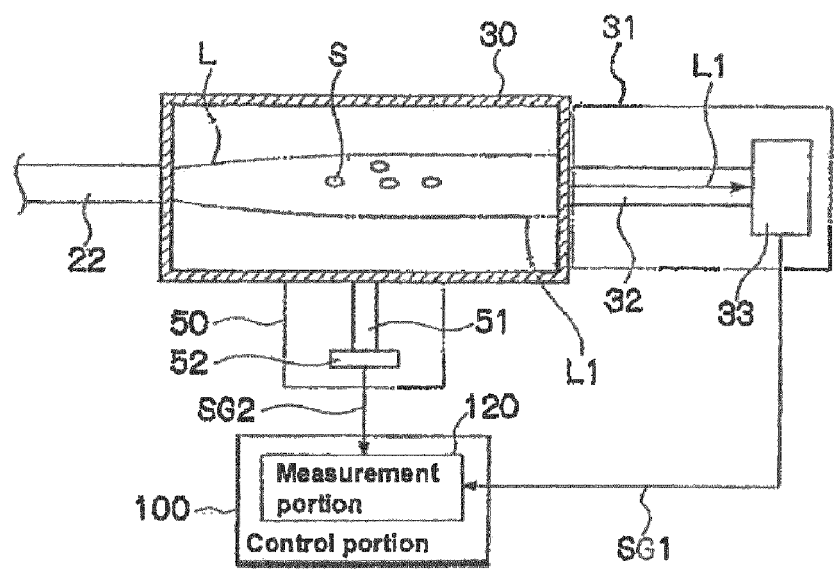
FIG. 2 is a cross sectional view along K-K line in FIG. 1.

FIGS. 1 and 2 depict a preferable embodiment of an optical measurement apparatus of the invention. FIG. 1 is a side view of the optical measurement apparatus of the invention. FIG. 2 is a cross sectional view along K-K line depicted in FIG. 1.

Structural examples of the optical measurement apparatus 1 depicted in FIGS. 1 and 2 are described.

The optical measurement apparatus 10 depicted in FIG. 1 is used as an optical measurement portion in the flow cyte meter for example. The flow cyto meter 1 includes the optical measurement apparatus 10, a supply portion 12 for supplying liquid in which a sample (minute object to be tested) is dispersed, and a dispensing portion 13 for dispensing the sample.

The supply portion 12 can supply the liquid 11 with the sample S dispersed through a tube 14 as the sample flow 11S together with a sheath flow 19 in a Z1 direction to the optical measurement apparatus 10 (from the upper side to the down side in the example in FIG. 1). The sample S in the liquid 11 passing through the capillary 30 of the optical measurement apparatus 10 can be divided into necessary substance and unnecessary substance in the dispensing portion 13.

The optical measurement apparatus 10 depicted in FIG. 1 includes a light source portion 20 for irradiating a irradiating light L to a sample flow 11s and the sample S in the capillary 30, a capillary 30 as a flow passage for flowing the sample flow 11S including the sample S, a light receiving portion 31 for receiving the transmitted light, a light receiving portion 50 for receiving side scattered light, and a control portion 100. The control portion is also called as an analyzing portion to analyze the size, shape and inner structure of the sample from a measurement signal.

The above described sample is also called as minute object. The single mode means an intensity pattern of Gaussian distribution. The optical measurement apparatus for measuring the optical information of the sample is also called as a sample measurement apparatus or minute object measurement apparatus which is an apparatus to measure the size, shape and inner structure of the sample.

The light source portion 20 of the optical measurement apparatus 10 irradiates the irradiating light L to the liquid 11 in the capillary 30, and the light receiving portion 31 receives the light receiving information L1 in an arbitrary region including the irradiating light L. The light receiving portion 31 sends a light receiving signal SG1 to the measurement portion 120. The measurement portion 120 analyzes the variation of the light receiving signal SG1 of the sample S to identify the size information, and the shape information such as shape recognition, cell recognition of the sample, for example.

The light source portion 20 comprises a laser light source 21 such as a laser diode and an optical fiber 22 for irradiation as an example. The light receiving portion 13 comprises an optical fiber 32 and a light receiving element 3 such as a photo diode, for example as depicted in FIG. 2. As depicted in FIG. 1, the first optical axis D1 of the light source portion 20 and the second optical axis D2 of the light receiving portion 31 are preferably identical.

In the optical measurement apparatus 10, the single mode pumping light (irradiating light) L generated by the laser light source 21 is irradiated to the sample flow 11S of the liquid 11 in the capillary 30 and the sample S passing in the sample flow 11S of the liquid 11 to measure the optical information (fluorescent information) of the sample S. More specifically, the irradiating light L of the light source portion 20 is irradiated to the sample flow 11S of the liquid 11 under the condition in which the relative position of the sample S to the irradiating varies at constant speed, and the optical information including the irradiating light L transmitting the sample flow 11S of the liquid 11 is received by the light receiving portion 31. The light receiving portion 31 sends the light receiving signal SG1 to the measurement portion 120.

The light receiving portion 50 for the side scattered light is positioned to the side of the capillary 30 to enable to receive the scattered light obtained from the sample flow 11S and sample S of the liquid 11.

The receiving light signal SG1 from the light receiving portion 31 and the receiving light signal SG2 from the light receiving portion 50 are processed in the measurement portion 120 of the control portion 100.

The sample S as depicted in FIGS. 1 and 2 is a cell of the size of 5 μm for example. The sample flow 11S is flown through the capillary of the optical measurement apparatus 10 in such manner that the sheath flow encompasses the sample flow 11S. The sheath flow technology lies in that the width of the sample flow 11S is arbitrarily controlled by the pressure difference of the sample flow 11S and the sheath flow 19 so as to reduce the failure pressure of the sample flow 11S and prevent from being clogged.

Here, an operational example of the optical measurement apparatus 10 depicted in FIGS. 1 and 2 is briefly described.

The supply portion 12 supplies the liquid 11 with the sample S dispersed through a tube 14 as the sample flow 11S together with a sheath flow 19 in a Z1 direction to the optical measurement apparatus 10 (from the upper side to the down side in the example in FIG. 1).

The irradiating light L generated by the laser light source 21 is irradiated to the sample flow 11S of the liquid 11 in the capillary 30 and the sample S passing in the sample flow 11S. The light in the arbitrary region including the irradiating light L transmitting the sample flow 11S is received as the optical information (transmitted light information) of the sample in the light receiving portion 31. In addition, the light receiving portion 50 for the side scattered light receives the scattered light and fluorescent light obtained from the sample flow 11S and the sample S. The receiving light signal SG1 from the light receiving portion 31 and the receiving light signal SG2 from the light receiving portion 50 are processed in the measurement portion 120 of the control portion 100. The control portion 100 controls the driving of the laser light source 21.

Figure 3:
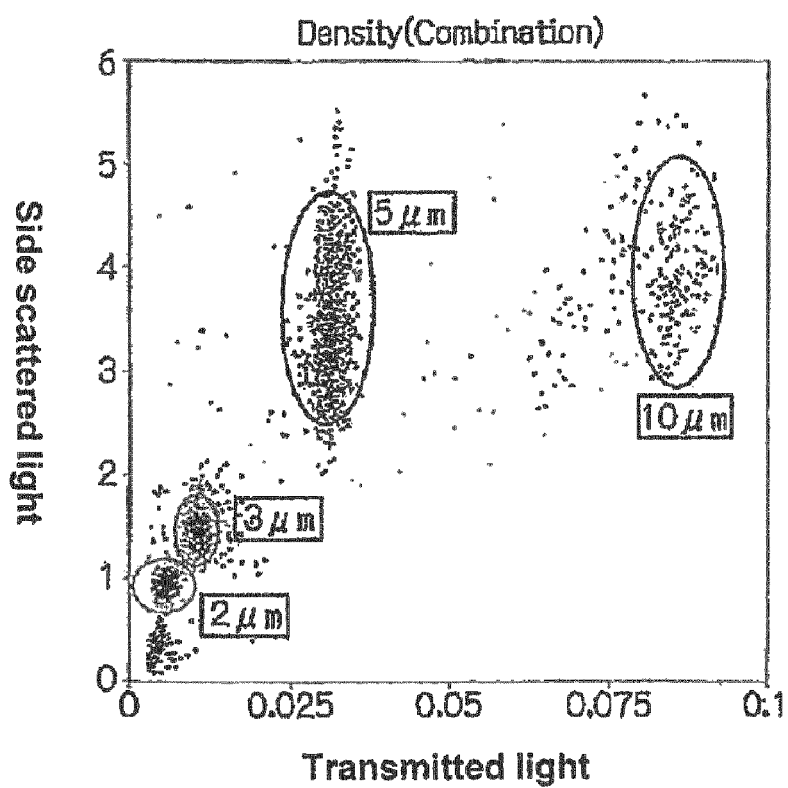
FIG. 3 shows side scattered light in the vertical axis and transmitted light in the horizontal axis.

In FIG. 3, the side scattered light is shown in the vertical axis and the transmitted light is shown in the horizontal axis. As depicted in FIG. 3, the transmitted light is not so spread and has small variations in comparison with the side scattered light. For example, FIG. 3 is a scatter plot which shows the side scattered light in the vertical axis and maximum value (peak value) of the variation as the transmitted light information in the horizontal axis from the result of measuring various sizes of the particles. It can be recognized that the respective distributions are separated according to the particles.

Figure 4:
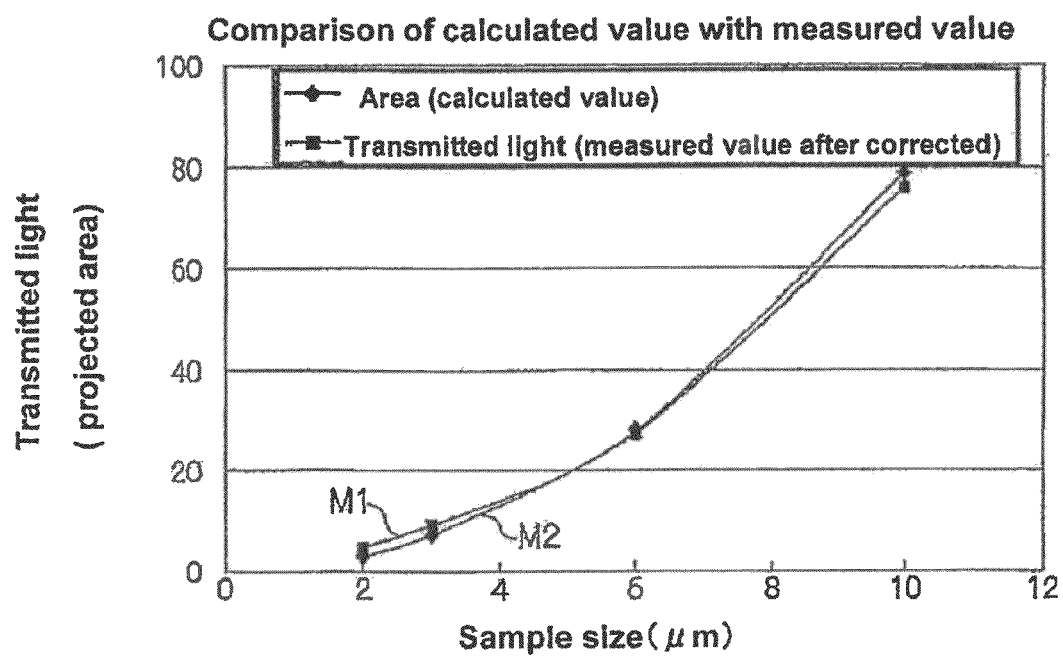
FIG. 4 depicts the curve M1 showing the transmitted light including the irradiating light actually received in the light receiving portion and the curve M2 of calculating value of the transmitted light for comparison.

FIG. 4 is a scatter plot which shows average values of respective distributions of the transmitted light information in the vertical axis and particle diameters in the horizontal axis. An approximate curve M1 obtained by the particle diameters and transmitted light measurement values, and an approximate curve M2 obtained by the particle diameters and particles area are shown for comparison therein. Since the curve M1 and the curve M2 which is the calculated value of the transmitted light is closely approximated, it can be said that there is correlation between the maximum value of the variation of the transmitted light and the diameter of the sample (projected area).

FIG. 4 depicts the curve M1, which shows the transmitted light including the irradiating light L1 actually received in the light receiving portion 31 depicted in FIG. 1, and the curve M2, which is the calculated value of the transmitted light, for comparison. The transmitted light (area value) is shown in the vertical axis, and the size of the sample S is shown in the horizontal axis. The curve M1 and the curve M2 which is the calculated value of the transmitted light is very closely approximated. There is correlation between the peak value of the transmitted light and the diameter of the sample (projected area).

FIG. 5 shows examples of the receiving light signal SG1 obtained in the light receiving portion 31 of the transmitted light depicted in FIG. 1. FIG. 5(A) is an example of the receiving light signal SG1 with zero distortion degree (normal distribution). FIG. 5(B) is an example of the distribution of the receiving light signal SG1 with a relation of distortion degree>zero. FIG. 5(C) is an example showing a relation of steepness degree>zero. FIG. 5(D) is an example of fitting analysis of the receiving light signal SG1. FIG. 5(E) is an example of peak correction of the receiving light signal SG1. FIG. 5(F) shows an example of the pulse pattern of the receiving light signal SG1, which has two extreme values. FIG. 5(G) shows an example of the analysis object portion 210 of the arbitrary region of the receiving light signal SG1. The noise is removed by the fitting and formed to be compensated.

Figure 6:
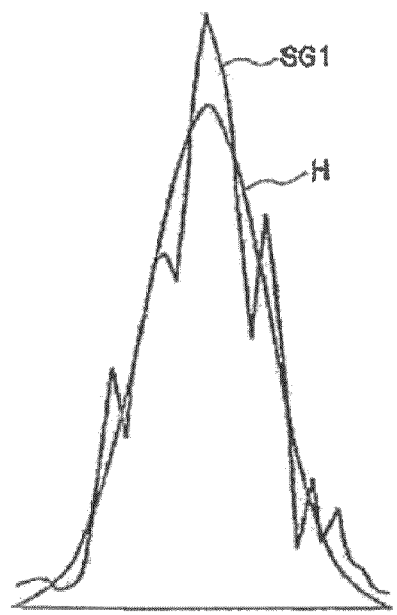
FIG. 6 shows an example of enlarged fitting analysis of the receiving light signal SG1 depicted in FIG. 5(D)

FIG. 6 shows an enlarged example of the fitting analysis of the receiving light signal SG1. FIG. 6 shows a shape example of the actual receiving light signal SG1, and a shape example of the fitting curve H showing the result of the fitting analysis of the receiving light signal SG1. The actual receiving light signal SG1 includes noise and has a non-smooth shape. In the drawing, the variation is reduced by obtaining the amount of characteristics from the fitting curve H in case that the peak value does not exist in the center position of the wave profile.

Figure 7:
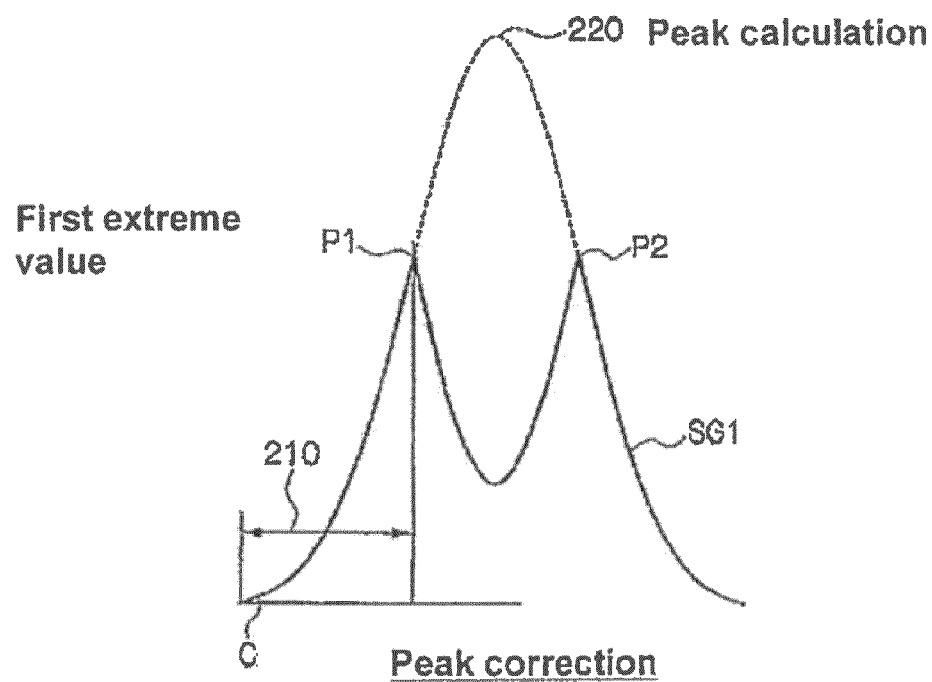
FIG. 7 shows an example in which the pulse shape of the receiving light signal SG1 does not have a single peak value, but have the first extreme value P1 and the second extreme value.

FIG. 7 shows the case in which the pulse shape of the receiving light signal SG1 does not have a single peak value but has the first extreme value P1 and the second extreme value P2, so that the correlation between the receiving light signal SG1 and the normal distribution is low. In this case, the peak value 220 depicted by the dotted line is estimated, calculated with the use of the approximate curve of the analysis object portion (from the foot portion C to the first extreme value P1) excluding the center position so as to be analyzed, thus enabling to reduce the variation of the receiving light signal SG1.

FIG. 8 shows an example of a spherical cell 300 as an example of the sample S. FIG. 9 shows an example of an elongated cell 310 as another example of the sample S.

Figure 8A:
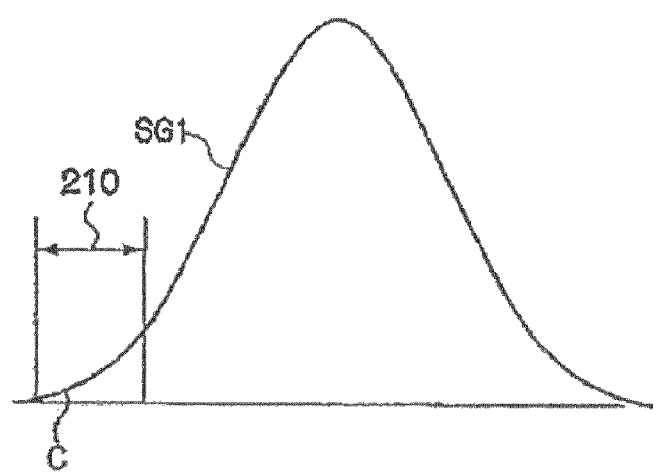
FIG. 8 shows an example of the spherical cell as the sample S.
Figure 8B:
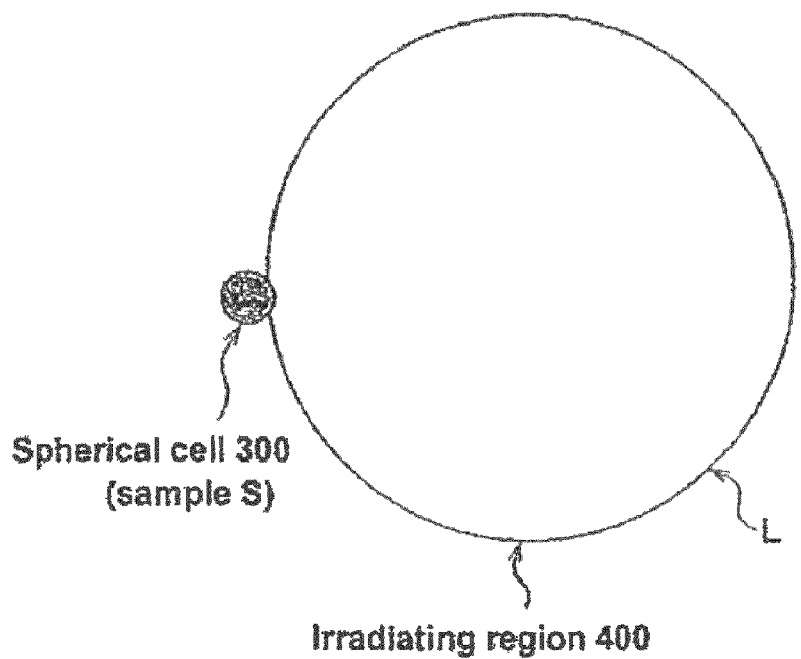

FIG. 8(A) depicts the receiving light signal SG1 in case that the spherical cell 300 is measured. FIG. 8(B) depicts the spherical cell 300 and an irradiating region 400 of the irradiating light L. In FIG. 8(B), since the irradiating region 400 is circular and the spherical cell 300 passes in the Z1 direction, the receiving light signal SG1 depicted in FIG. 8(A) is obtained.

Figure 9A:
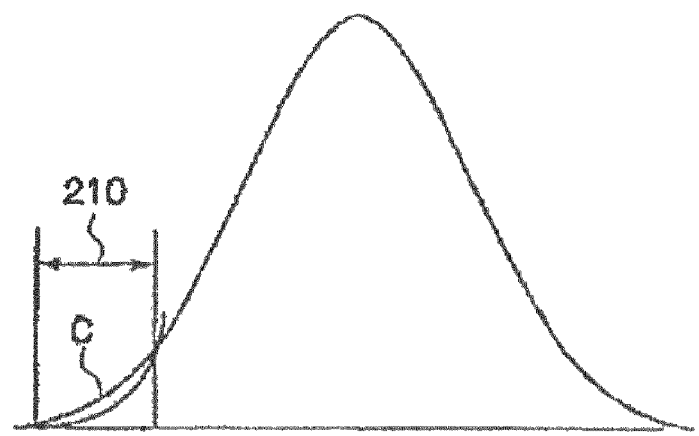
FIG. 9 shows an example of the elongated cell as the sample S.
Figure 9B:
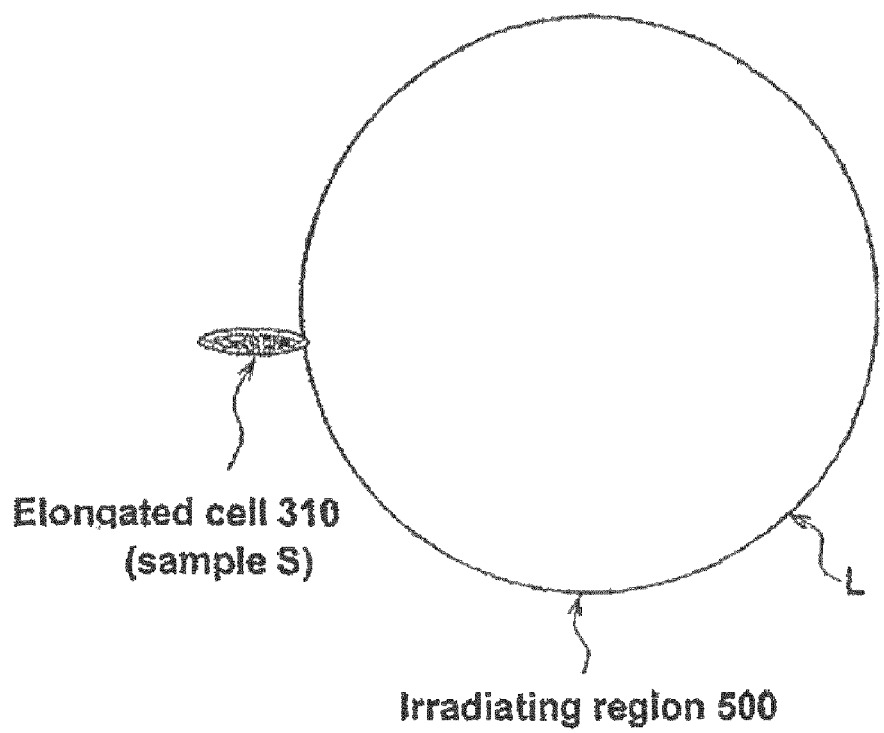

In the similar manner, FIG. 9(A) depicts the receiving light signal SG1 in case that the elongated cell 310 is measured. FIG. 9(B) depicts the elongated cell 310 and an irradiating region 500 of the irradiating light L. In FIG. 9(B), since the irradiating region 500 is circular and the elongated cell 310 passes in the Z1 direction, the receiving light signal SG1 depicted in FIG. 9(A) is obtained.

The analysis object portion 210 of the receiving light signal depicted in FIG. 8(A) and the analysis object portion 210 of the receiving light signal depicted in FIG. 9(A) are compared. Even if the spherical cell 300 and the elongated cell 310 have the same volume, the shape of the spherical cell 300 is different from the shape of the elongated cell 310. Thus, the inclinations of the pattern at the respective rising edge and the trailing edge in the analysis object portion 210 of the receiving light signal SG1 depicted in FIG. 8(A) are different from the inclinations of the pattern at the respective rising edge and the trailing edge in the analysis object portion 210 of the receiving light signal SG1 depicted in FIG. 9(A), when the spherical cell 300 and the elongated cell 310 enter into the irradiating regions 400, and 500 respectively, and when the spherical cell 300 and the elongated cell 310 leave the irradiating regions 400, and 500 respectively. However, it can be recognized that the same patterns appear after the spherical cell 300 and the elongated cell 310 enter into the respective irradiating regions 400, 500. The sizes of the irradiating regions 400, 500 are identical.

Figure 10:
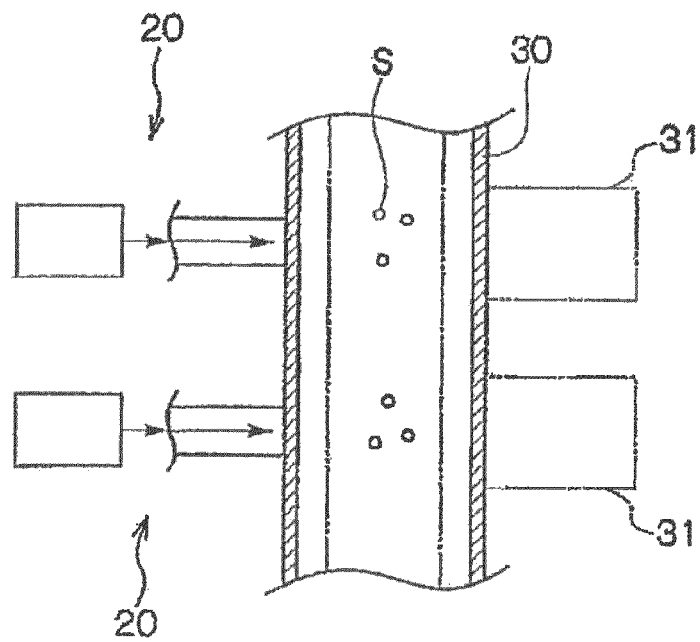
FIG. 10 depicts other embodiment of the invention.

FIG. 10 depicts other embodiment of the invention, which is different from the embodiment depicted in FIG. 1 in that a plurality of light source portions 20 and the corresponding light receiving portions 31, i.e., two sets 211, 212, are arranged. Laser lights having different wavelengths can be irradiated to the samples S in the liquid 11 in the respective set 211 comprising the light source portion 20 and the light receiving portion 31 and the set 212 comprising the light source portion 20 and the light receiving portion 31. More specifically, when the wavelength of the irradiating light generated by the light source portion is varied at least two types, the independent optical information can be obtained respectively. Thus, the sample is analyzed according to the variation of the wave profile to the wavelength, to enable to identify the sample S. The kind of the sample can be determined with certainty.

Incidentally, the light irradiated from the light source portion to the liquid and the cell or the like as the object to be measured (sample) is called as the irradiating light. The irradiating light transmitting the cell as the object to be measured (sample) is called as the transmitted (transmitting) light, thus discriminating those lights. The wavelength of the transmitting light is applicably from 325 nm to 900 nm. The wavelength of the transmitting light is desirably 635 nm or 488 in particular.

Figure 11:
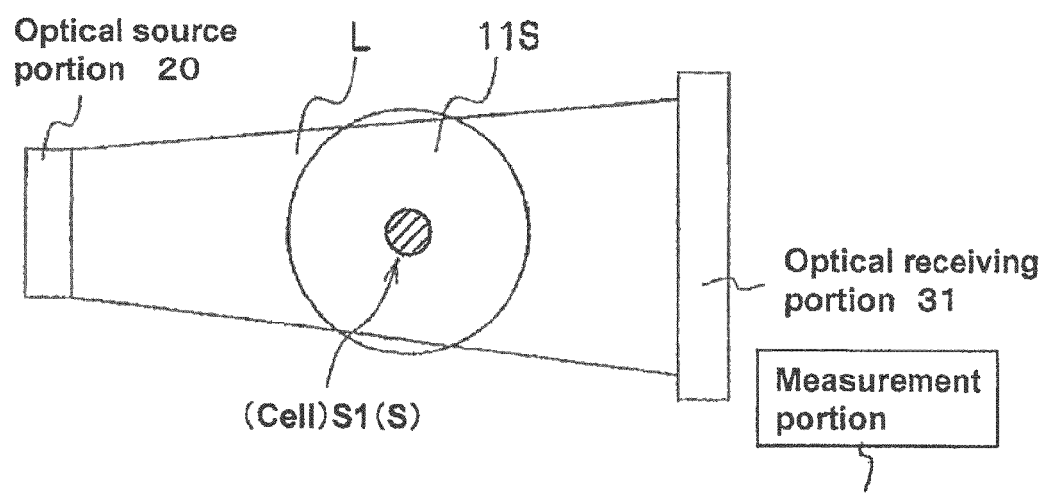
FIG. 11 shows the state that the irradiating light from the light source portion expands.

As depicted in FIG. 11, in the embodiment of the invention, the irradiating light L is irradiated from the light source portion 20, for example, the laser light source to the liquid or the sample S such as the cell S1. The irradiating light L expands from the light source portion 20 toward the light receiving portion 31. As the light receiving element for the light receiving portion 31, a photomultiplier tube, CCD (charge-coupled device), photodiode or the like is applicable. The irradiating light irradiated from the light source portion to the cell is in parallel or expands from the light source portion to the light receiving portion.

In the embodiment of the measuring method of the invention, as depicted in FIG. 11, the irradiating light L is irradiated to the cell S1 in the liquid 11S flowing in the flow passage, and the transmitted light passing through the cell in the liquid is received, and thus the optical information of the cell S1 is measured. The irradiating light L is irradiated from the light source portion 20 to the cell S1, and the irradiating light L is irradiated from the light source portion 20 to the liquid under the condition in which the relative position of the cell S1 to the irradiating light L varies at constant speed along the direction perpendicular the paper plane in FIG. 11. Then, the phenomenon that the intensity of the transmitted light varies in terms of time is measured by the measuring portion 120 at the time when the transmitted light is received in the light receiving portion 31 and the receiving light signal is generated. According to the above, the kind of the cell 51 can be determined based on the variation in terms of time of the intensity in the transmitted light.

At the time of the measurement, both of the attenuation and the amplification of the intensity in the transmitted light are measured. The intensity of the transmitted light varies over time depending on the cell species or number of the cell nucleus, and the wave profile has at least two attenuated wave profile portions. The intensity of the transmitted light varies over time depending on the cell species or number of the cell nucleus, and the wave profile has repetitive attenuated wave profile portions and amplified wave profile portions. The intensity of the transmitted light varies in terms of time depending on the attribution and the property of the cell expressed by the number of the cell nucleus and the size of the cell nucleus.

The irradiating light is irradiated to the cell in the liquid, and the transmitted light transmitting through the cell in the liquid is received. At the time of measurement of the optical information of the cell, the irradiating light is irradiated from the light source portion to the cell, and the irradiating light is irradiated from the light source portion to the liquid under the condition in which the relative position of the cell to the irradiating light varies at constant speed. Then, the transmitted light is received in the light receiving portion. The wave profile of the transmitted light with the intensity varied over time is approximated to one or plurality of the standard template wave profile prepared in advance so as to be separated in layer, thus the property of the cell can be specified.

According to the wave profile varied over time with the use of the intensity of the transmitted light, in which the attenuated wave profile portion and the amplified wave profile portion are repeated, the kind of the cell or cancer cell representing different property from the same kind of cell is specified. A kind of particular cell, B kind of particular cell, or B kind of particular cell in the C kind of particular cell is specified. In addition, an abnormal cell in the A kind of particular cell is specified as the cancer cell. The intensity of the transmitted light enables to specify the particular cell including the blood cells. The wavelength of the transmitted light is from 325 nm to 900 nm.

The result of the measurement of the transmitted light wave profile obtained by a plurality of cells is separated in layer into the plurality of kinds of wave profiles. The kind of the cell and the state of the cell are specified from the statistical information over the whole kinds. The amplification of the transmitted light means the variation over time of the intensity of the transmitted light which is measured by the phenomenon that the interference phenomenon of the transmitted light is caused to occur according to the attribution and the property such as the size of the cell, the number and the size of cell nucleus. According to the above specification results, arbitral sample can be separately collected in the evaluation method of the cell. The specified cell is dispensed to be selected as the method for obtaining the cell. The selected cell is cultivated or a prescribed reagent is added to the selected cell so as to evaluate the variation of the selected cell over time.

For example, FIG. 12 shows an example of the wave profile of the receiving light signal SG1 depicted in FIG. 1 in case that the transmitted light is received.

Figure 12A:
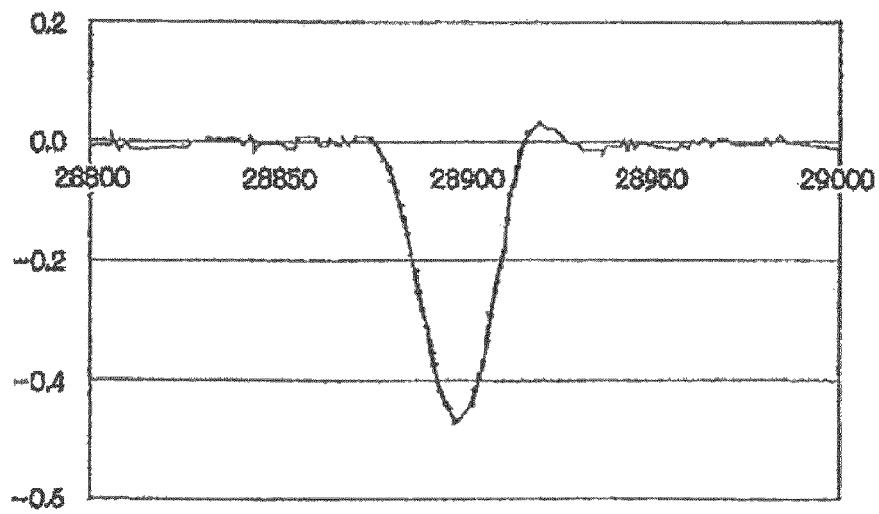
FIG. 12 shows an example of the wave profile of the receiving light signal when the transmitted light is received.

FIG. 12(A) shows the pattern wave profile of the transmitted light having a general single peak. The pattern wave profile of the transmitted light having a general single peak is the data of the attenuated wave profile of the intensity of the transmitted light of the impermeable beads and some kind of cell, which is the single peak wave profile having one downward protruding portion. In this case, there is one valley of the wave profile which is the signal corresponding to the general forward scattering.

Figure 12B:
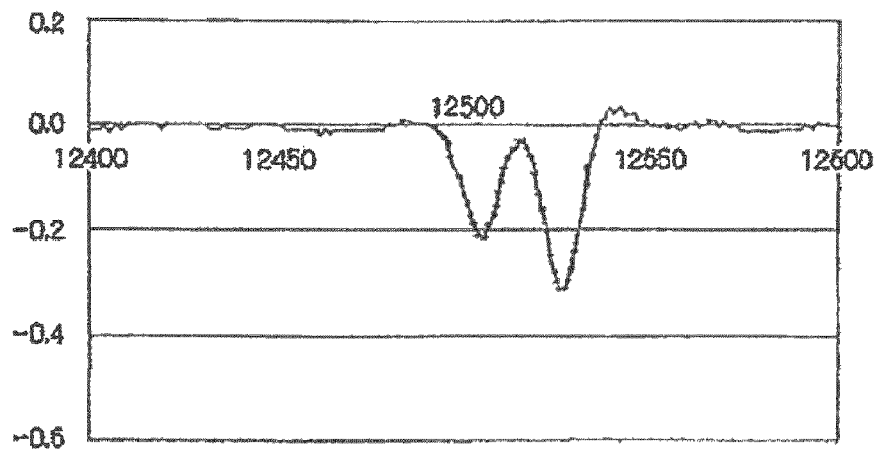
Figure 12C:
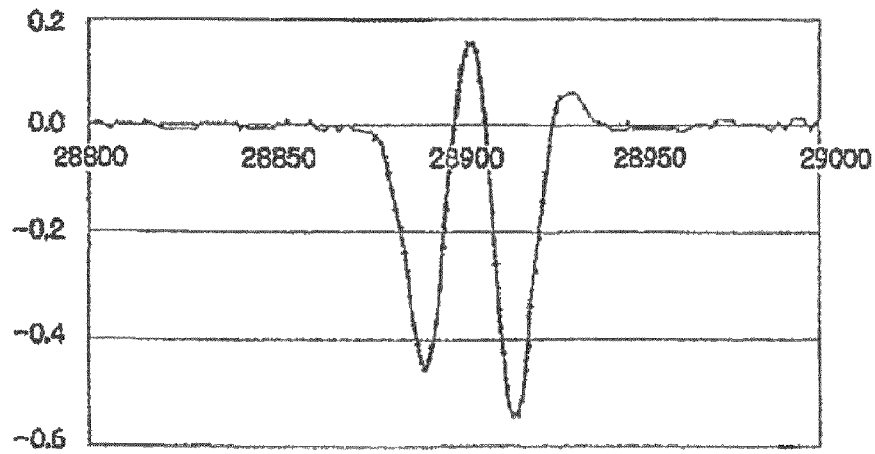

FIGS. 12(B) and 12(C) show examples of the pattern wave profile (multiple peaks) of the transmitted light confirmed by the cell, which are frequently confirmed by the cell of the mouse, for example. When the transmitted light is received, the pattern wave profile of the transmitted light is different depending on the kind of the cell S1 as the sample S. In this case, the wave profile has two valleys and one mountain, which may be caused by the variation of the inner state of the cell, although the wave profile should be like that depicted in FIG. 12(A) in a normal situation.

The pattern wave profile of the transmitted light depicted in FIG. 12(B) is a multi-peak wave profile having two downward protruding portions, which shows the intensity of the transmitted light of the cell representing varied wave profile of the attenuation according to the optical phenomenon such as interference.

In addition, the pattern wave profile of the transmitted light depicted in FIG. 12(C) is a multi-peak wave profile having two downward protruding portions, which shows the intensity of the transmitted light of the cell representing further varied wave profile of the attenuation according to the optical phenomenon such as interference in comparison with the pattern wave profile of the transmitted light depicted in FIG. 12(B).

The pattern wave profiles of the transmitted light depicted in FIGS. 12(B) and 12(C) are obtained. Thus, the intensity of the transmitted light is formed by at least two attenuation wave profiles according to the number of the cell nucleus representing cell species. The intensity of the transmitted light is formed by the repletion of the attenuated wave profile and the amplified wave profile over time according to the number of the cell nucleus representing cell species. The intensity of the transmitted light varies in terms of time depending on the attribution and the property of the cell expressed by the number of the cell nucleus and the size of the cell nucleus.

The pattern wave profile is obtained. Thus, the intensity of the transmitted light is expressed as a single peak wave profile and is attenuated for the impermeable beads or a certain kind of cell, as the pattern wave profile of the transmitted light as depicted in FIG. 12(A). Contrary to the above, the intensity of the transmitted light shows the behavior of repetitive attenuated wave profile and amplified wave profile in the pattern wave profiles depicted in FIGS. 12(B) and 12(C).

In the embodiment of the measuring method of the invention, the irradiating light is irradiated to the cell in the liquid flowing in the flow passage, and the transmitted light passing through the cell in the liquid is received, and thus the optical information of the cell is measured. The irradiating light L is irradiated from the light source portion 20 to the cell S1, and the irradiating light L is irradiated from the light source portion 20 to the liquid under the condition in which the relative position of the cell S1 to the irradiating light L varies at constant speed. Then, the phenomenon that the intensity of the transmitted light varies in terms of time is measured by the measuring portion 120 at the time when the transmitted light is received and the receiving light signal is generated. According to the above, the property of the cell can be determined by approximating the wave profile of the intensity of the transmitted light varied in terms of time to a standard template wave profile prepared in advance. The intensity of the transmitted light is formed by repeating attenuated wave profile and amplified wave profile over time, and the kind of the cell or cancer cell representing different property from the same kind of cell is specified. The specified cell is dispensed to be selected. The selected cell is cultivated or a prescribed reagent is added to the selected cell so as to evaluate the variation of the selected cell over time.

With the use of the intensity of the transmitted light, A kind of particular cell, B kind of particular cell, or B kind of particular cell in the C kind of particular cell is specified. In addition, with the use of the intensity of the transmitted light, the cell in the blood cells is specified.

Figure 13A:
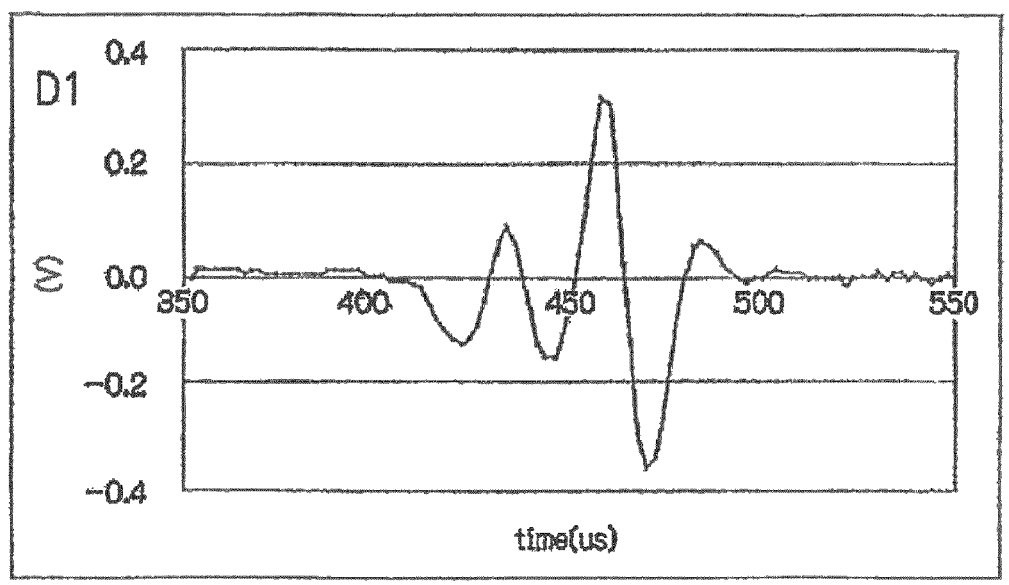
FIG. 13 shows another example of the wave profile of the receiving light signal when the transmitted light is received.
Figure 13B:
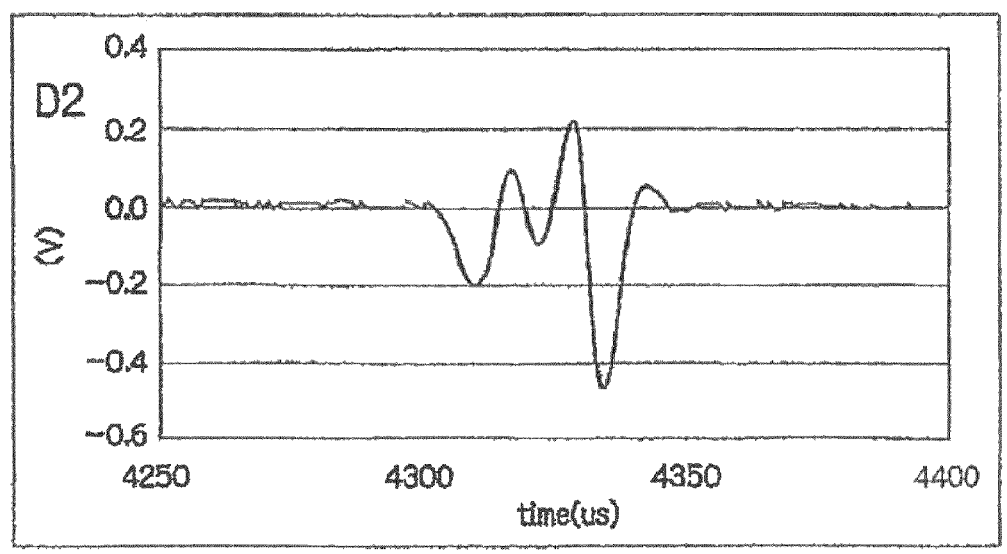

FIG. 13 shows an example of another wave profile of the pattern wave profile of the transmitted light in case that the transmitted light is received. FIGS. 13(A) and 13(B) respectively show the pattern wave profiles (multiple peaks) D1, D2 of the transmitted light obtained by the cell likely to be a cancer cell. The pattern wave profiles D1, D2 of the transmitted light have at least three attenuated wave profiles and amplified wave profiles, respectively. Those pattern wave profiles of the transmitted light have a plurality of attenuated wave profiles and amplified wave profiles according to the optical phenomena such as interference.

Figure 14:
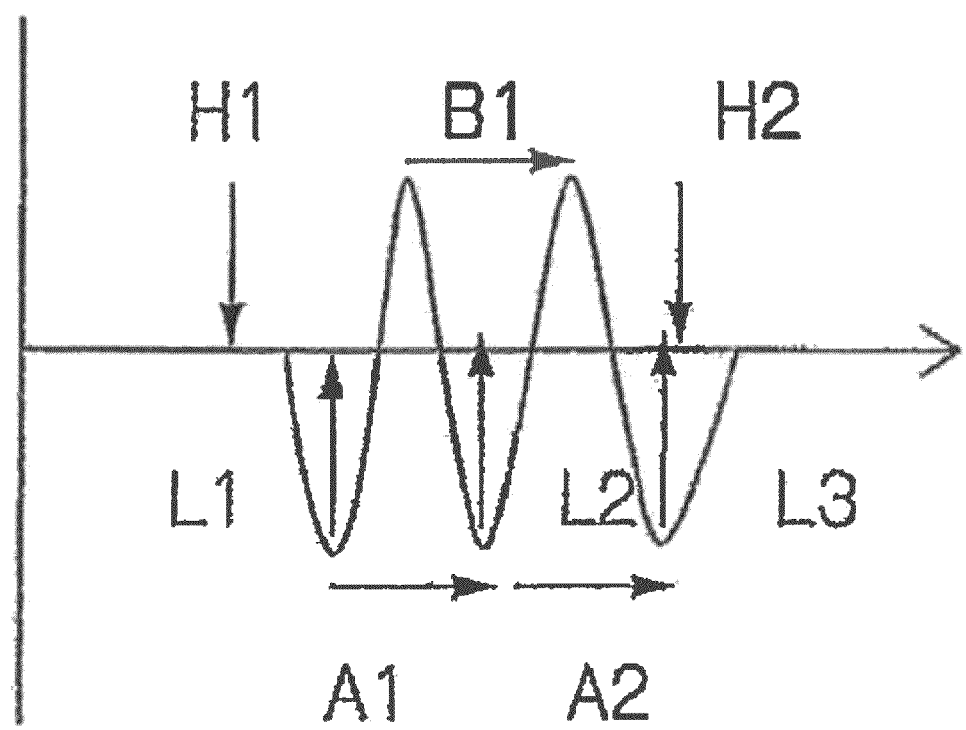
FIG. 14 shows an example of the standard template prepared in advance.

FIG. 14 shows an example of a standard template wave profile D (wave profile for comparative analysis) prepared in advance to specify the property of the cancer cell in a certain kind of cells to be measured. The standard template wave profile includes a plurality of parameters H1, H2, L1, L2, L3, A1, A2, B1 or the like for calculation.

The pattern wave profiles D1, D2 of the transmitted light according to a certain kind of cells depicted in FIGS. 13(A) and 13(B) are actually measured. The processing belonging to the standard template wave profile D prepared in advance is carried out at high speed to the actually measured pattern wave profiles D1, D2 of the transmitted light. Thus, the property of the cancer cell can be specified in the certain kind of cells. More specifically, the normal cell and the cancer cell can be discriminated in the certain kind of cells. The wave profiles depicted in FIGS. 13(A) and 13(B) have three valleys and two mountains respectively. The properties thereof are different, although the numbers of the valley and mountain are the same. When the frequency analysis of the wave profile is applied, the peak position of the power spectrum varies so as to specify the wave profile in analog manner. When the operation is carried out by the number of the valley and mountain, the wave profile is specified in digital manner.

According to the intensity of the transmitted light, a specific cell including the blood cell can be specified.

The light receiving portion comprises a CCD (charge-coupled device) camera, as described above. The cell flowing in the narrow flow passage or the cell stationing in the liquid can be measured by the variation of stopping of the relative position of the cell, irradiating portion and the light receiving portion. Thus, the intensity of the transmitted light can be measured by the variation of stopping of the relative position of the cell, irradiating portion and the light receiving portion, when the cell flows in the narrow flow passage or the cell stations in the liquid.

Figure 15A:
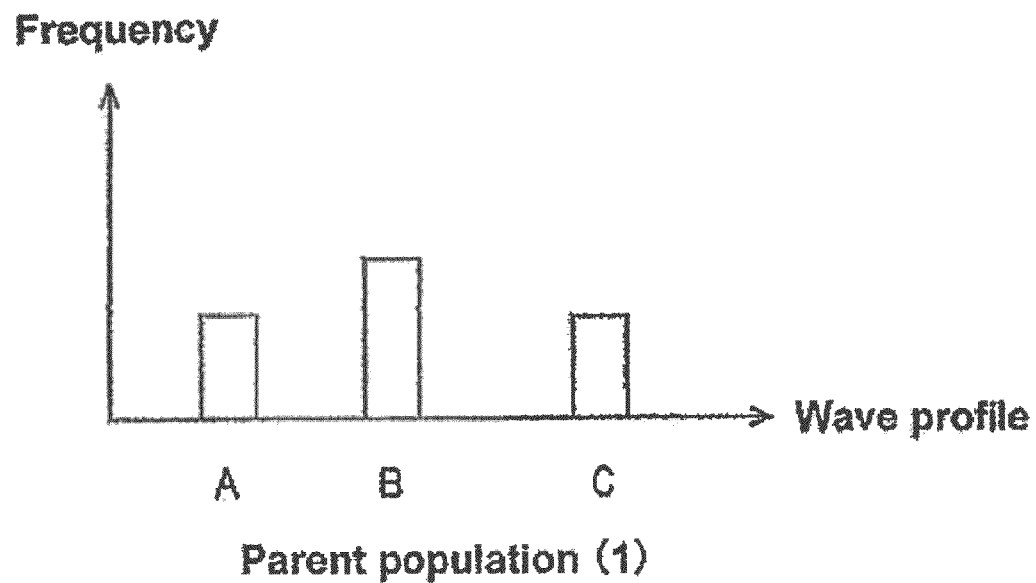
FIG. 15 shows the parent population (1) and the parent population (2) of the cell A, B, and C.
Figure 15B:
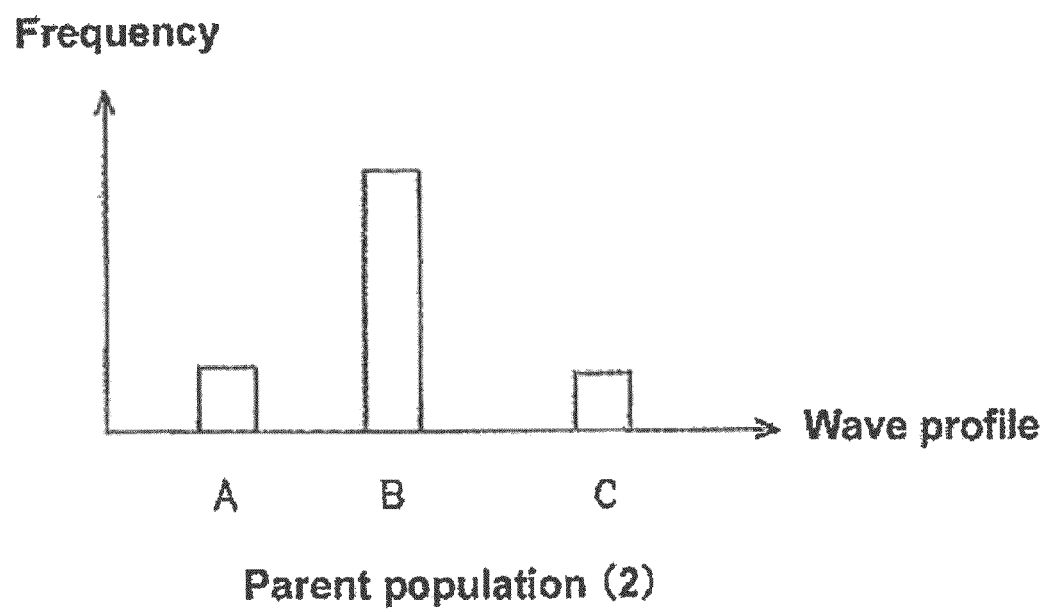

The varied wave profiles of the intensity of the transmitted light to the cell in the parent population are divided into a plurality of groups. The cell is distinguished from the parent population and evaluated with the frequency distribution of the respective groups. FIG. 15 shows the parent population (1) and the parent population (2) of the cells A, B, and C as one example. The distribution of the wave profiles of the cells A, B, C in the parent population (1) is different from the distribution of the wave profiles of the cells A, B, C in the parent population (2), as depicted in FIG. 15. Thus, the cells in the parent population (1) are different in the state from the cells in the parent population (2). The state of variation of the cells in the parent population (1) can be reflected over time by means of adding a certain kind of reagent to the cells in the parent population (1).

Conventionally, the cell recognition and analysis are implemented by the nuclear staining of the cell, or the antigen, antibody response on the cell surface. However, there is a defect that the nuclear staining of the cell kills the cell. The cell is damaged by the antigen or antibody response, and in addition, the cell cannot be recognized if there is no antibody, thus being problematic.

Since the cell can be recognized or analyzed without staining in the embodiments of the invention, it is inevitably applied in such case that the cell is cultivated, or the variation of the cell is evaluated over time by medicine or the like.

In the embodiments of the invention, the transmitted light means the light passing through the cell, including diffracted light and scattered light. In the embodiments of the invention, the wave profile representing variation over time of the intensity of the transmitted light is called as a variation pattern of the intensity of the transmitted light. In the embodiments of the invention, the irradiating light from the light source portion is the light irradiated to the cell.

When the cell is measured, the variation over time of the intensity of the transmitted light to the cell is recognized as a wave profile pattern, and the variation over time of the intensity of the transmitted light to the cell is considered to be the feature amount of the wave profile pattern based on the number of the wave profile and the relation between the valley and mountain of the wave profile. The feature amount of the wave profile pattern is determined based on the result of the frequency analysis of the wave profile pattern. More specifically, as the feature amount of the wave profile pattern, the maximum value or peak value of the power spectrum, the number of the peak value or the ratio is used. When the cell is analyzed, the feature amount of the wave profile pattern, the cell species, the inner state of the cell, the number of cell nucleus or the state of the nucleus can be discriminated.

The measuring means such as the light receiving portion is arranged at the position in which the pumping light and at least the light transmitting the cell (all those light is called as a whole as the transmitted light) can be measured. In this case, the measuring means such as the light receiving portion is arranged at the position in which the pumping light, the light transmitting the cell, and the reflected light or forward scattered light (all those light is called as a whole as the transmitted light) can be measured. The above described measuring means comprises an optical fiber, in which the core portion of the optical fiber is smaller than the pumping light spot of the measuring means of the transmitted light.

The kind of the cell or cancer cell representing different property from the same kind of cell is analyzed with the use of the information of the measurement of the wave profile pattern of the transmitted light. In this case, the feature amount of the wave profile pattern is extracted from the information of the measurement of the wave profile pattern of the transmitted light. The kind of the cell or cancer cell representing different property from the same kind of cell is analyzed with the use of the feature amount.

A specific cell is recognized in a plurality of cells, or the cell having different inner state is recognized in the same cells, with the use of the information of the measurement of the wave profile pattern of the transmitted light. For example, the cancer cell is recognized in a plurality of cells, or the cancer cell having different inner state is recognized in the same cancer cells, with the use of the information of the measurement of the wave profile pattern of the transmitted light.

The inner state of the cell includes not only the attribution and property of the cell such as the size of the cell, the number and the size of the cell nucleus, but also the state of the protein in the cell cytoplasm or the state of other structure, or the like. The interference phenomena of the transmitted light is caused by the size of the cell, the number and the size of the cell nucleus, state of the protein in the cell cytoplasm or the like.

The light receiving portion comprises a CCD (charge-coupled device) camera, for example. In either state of that the cell flowing in the narrow flow passage or the cell is stationed in the liquid, the intensity of the receiving light signal and the two dimensional distribution state of the intensity of the receiving light signal can be measured by the stationing or varying of the relative position among the cell, the irradiating portion and the light receiving portion.

In the embodiments of the invention, the irradiating light (incident light) generated by the light source portion is the parallel or approximately parallel light (the range up to the expanding angle of the numerical aperture (NA) of the optical fiber). The detecting light detected in the light receiving portion can use the transmitted light information and the scattered light information including the side scattered light and the backward scattered light. The transmitted light is the light information measured at the position in which the irradiating light (incident light) can be directly measured.

The variation of the receiving light signal, i.e., the variation of the transmitted light is the signal variation over time when the sample S passes the irradiating region, under the condition that the receiving light signal value of the irradiating light L which is directly received is the standard, when the sample S does not exist in the irradiating region. When the sample S enters into the irradiating region, the received light amount in the irradiating light L varies by the scattering, absorbing, transmitting (including the diffraction and interference). For example, supposing that the sample is a heterogeneous material. Since the irradiating light has the normal distribution intensity pattern (single mode), the receiving light signal becomes minimum when the sample is positioned in the irradiating region, thus obtaining the pulse shaped signal variation with a single peak. The size of the sample can be identified by the peak value.

The sample S to be measured is the biological body such as cell, particle, bacteria, or inorganic substance flowing in the flow passage.

The transmitted light information and/or the scattered light information are processed to enable to obtain the information such as the size and the inner structure of the sample S. As the irradiating light, the single mode light is irradiated. The optical information including the irradiating light transmitting the liquid is detected in the light receiving portion, and the kind of the sample S is determined from the variation of the wave profile (variation of frequency component) over time of the receiving light signal SG1, or from the detection of the variation from the standard wave profile.

In the embodiment of the invention, the irradiating light is irradiated to the liquid in the capillary 30 as a flow cell, and arbitrary region including the irradiating light is received in the light receiving portion so that the light receiving portion generates the receiving light signal SG1. The preciseness of the size information is improved, and the recognition of the shape and the recognition of the cell are implemented by analyzing the variation of the receiving light signal SG1 by the sample S.

The light measurement apparatus of the invention, in which the light is irradiated to the sample dispersed in the liquid flowing through the flow passage, is used for measuring optical information of the sample. The apparatus includes a light source portion 20 for irradiating the irradiating light L to the liquid 11, a light receiving portion 31 to receive the optical information of the sample S including the irradiating light transmitted through the liquid to generate a receiving light signal SG1, under a condition in which the liquid is irradiated by the irradiating light of the light source portion 20 in a state that a relative position of the sample S to the irradiating light varies at constant speed, a measurement portion 120 for measuring variation of the receiving light signal according to the sample. According to the above, shape information of the sample (size, kind of the cell, contour such as circle elongated shape) can be precisely measured. Arbitrary sample can be sorted from the result of the identification.

In the light measurement apparatus, the sample S is dispersed in the liquid flowing through the flow passage. According to this, the relative position of the sample S to the irradiating light is varied at constant speed by simply flowing the liquid through the flow passage.

In the light measurement apparatus, the irradiating light L for measurement is a non-converging light irradiated through an optical fiber 22. According to this, the irradiating light can be irradiated to the sample S in arbitrary region in the liquid.

In the light measurement apparatus, the irradiating light L transmitting the liquid is received by the optical fiber 32. According to this, the irradiating light L including the optical information of the sample S can be surely received in the light receiving portion 31 with the use of the optical fiber 32.

In the light measurement apparatus, the variation of the receiving light signal SG1 according to the sample S is the variation of the receiving light signal SG1 according to a phenomenon that the relative position of the sample S to the irradiating light L varies at constant speed. According to this, the shape of the sample S can be precisely obtained.

In the light measurement apparatus, a variation pattern of the receiving light signal SG1 according to the sample S is analyzed. According to this, the difference of the sample S can be surely identified.

In the light measurement apparatus, a maximum value, width, or area of a pulse shape portion in the variation pattern of the receiving light signal is measured.

In the light measurement apparatus, the sample size is identified by the maximum value of the pulse shape portion in the variation pattern of the receiving light signal.

In the light measurement apparatus, the sample is analyzed by statistical information of an approximate curve of the pulse shape portion in the variation pattern of the receiving light signal.

In the light measurement apparatus, the receiving light signal is pattern-analyzed with the pulse shape portion.

In the light measurement apparatus, a plurality of peak values are corrected from a variation pattern to analyze a single pulse approximate curve in the receiving light signal.

In the light measurement apparatus, an arbitrary region of a variation pattern is information-analyzed to identify a shape of the sample in the receiving light signal.

In the light measurement apparatus, the sample is analyzed from the receiving light signal of a plurality of wavelengths.

In the light measurement apparatus, a variation pattern is analyzed to identify a kind of the cell in the receiving light signal.

In the light measurement apparatus, a specific region in an arbitrary phase of a cell cycle or a region of polyploid nucleus of the sample is recognized.

In the light measurement apparatus, a size, shape and/or inner structure of the sample is identified from a plurality of information analyzing a variation pattern of the transmitted light.

In the light measurement apparatus, a plurality of light receiving portions receiving the transmitted light is included.

In the light measurement apparatus, fluorescent information of the sample and a receiving light signal of a side scattered light.

In the light measurement apparatus, an arbitrary sample is dispensed according to a result of identification.

The present invention is not limited to the above described embodiments. Various modification can be applied thereto.

The light source portion 20 depicted in FIG. 1 may be comprised by the optical fiber 22 and the laser light source 21, or may be comprised only by the laser light source 21. The light receiving portion 31 of the transmitted light may be comprised by the optical fiber 32 and the light receiving element 33, or may be comprised only by the light receiving element 33. The light receiving portion 50 of the side scattered light may be comprised by the optical fiber 51 and the light receiving element 52, or may be comprised only by the light receiving element 52. As for the light receiving portion 50 of the side scattered light, the lens system may be used in place of the optical fiber 51.

Although the capillary 30 depicted in FIGS. 1 and 2 is a hollow member having a cross section of square for example, the capillary may have the cross section of rectangle or other shape for example.

The optical measurement apparatus of the invention is applicable to such various fields as the field in which examination, analysis and break down is required concerning such biological polymer as gene, immune system, protein tyrosine, amino acid, sugar group, for example, engineering field, general agronomy such as food, agricultural commodity, sea food processing or the like, pharmaceutical field, medicine field such as sanitation, health, immune, epidemic, heredity or the like, science field such as chemistry, biology or the like.

According to the light measurement apparatus and light measurement method of the invention, the shape information of the sample can be precisely measured.

According to the light measurement method of the invention, the kind of the cell can be determined.

What is claimed is:

1. An optical measurement apparatus for measuring an optical information of a sample by irradiating a single mode light to the sample dispersed in a liquid, which comprises:
   a light source portion that irradiates the irradiating light to the liquid;
   a light receiving portion that receives the optical information of the sample including the irradiating light transmitted through the liquid to generate a receiving light signal, under a condition in which the liquid is irradiated by the irradiating light of the light source portion in a state that a relative position of the sample to the irradiating light varies at constant speed;
   a measurement portion that measures attenuation and amplification of intensity of the receiving light signal according to the sample; and
   a control portion that analyzes at least one of a size, shape and internal structure of the sample from the measured signal.

2. The optical measurement apparatus according to claim 1, wherein the irradiating light for measurement is a non-converging light irradiated through an optical fiber.

3. The optical measurement apparatus according to claim 2, wherein the irradiating light transmitting the liquid is received by the optical fiber.

4. The optical measurement apparatus according to claim 1, wherein the control portion analyzes a variation pattern of the receiving light signal according to the sample.

5. The optical measurement apparatus according to claim 4, wherein the control portion measures a maximum value, width, or area of a pulse shape portion in the variation pattern of the receiving light signal.

6. The optical measurement apparatus according to claim 4, wherein the control portion identifies the sample size by the maximum value of the pulse shape portion in the variation pattern of the receiving light signal.

7. The optical measurement apparatus according to claim 4, wherein the control portion analyzes the sample by statistical information of an approximate curve of the pulse shape portion in the variation pattern of the receiving light signal.

8. The optical measurement apparatus according to claim 4, wherein the control portion pattern-analyzes the receiving light signal the pulse shape portion.

9. The optical measurement apparatus according to claim 1, wherein the control portion corrects a plurality of peak values from a variation pattern and analyzes a single pulse approximate curve in the receiving light signal.

10. The optical measurement apparatus according to claim 1, wherein the control portion information-analyzes an arbitrary region of a variation pattern to identify a shape of the sample in the receiving light signal.

11. The optical measurement apparatus according to claim 1, wherein the control portion analyzes the sample from the receiving light signal of a plurality of wavelengths.

12. The optical measurement apparatus according to claim 1, wherein the control portion analyzes a variation pattern to identify a kind of the cell in the receiving light signal.

13. The optical measurement apparatus according to claim 1, wherein the control portion recognizes a specific region in an arbitrary phase of a cell cycle or a region of polyploid nucleus of the sample.

14. The optical measurement apparatus according to claim 1, wherein the control portion identifies at least one of a size, shape and inner structure of the sample from a plurality of information analyzing a variation pattern of the transmitted light.

15. The optical measurement apparatus according to claim 1, further comprising:
    a plurality of light receiving portions receiving the transmitted light.

16. The optical measurement apparatus according to claim 15, wherein the plurality of light receiving portions receive fluorescent information of the sample and a receiving light signal of a side scattered light.

17. The optical measurement apparatus according to claim 1, further comprising:
    a dispensing portion that dispenses an arbitrary sample according to a result of identification.

18. A light measurement method in which a irradiating light is irradiated to a cell in a liquid and a transmitted light transmitting the liquid and the cell is received to measure optical information of the cell, comprising:
    irradiating the irradiating light to the cell from a light source portion;
    irradiating the irradiating light from the light source portion to the liquid under a condition in which a relative position of the sample to the irradiating light varies at constant speed; and
    measuring attenuation and amplification of intensity of the transmitted light over time when the transmitted light is received to generate receiving light signal.

19. The light measurement method according to claim 18, wherein the intensity of the transmitted light varies depending on cell species or number of cell nucleus to have a wave profile including at least two attenuated wave profile portions.

20. The light measurement method according to claim 18, wherein the intensity of the transmitted light varies depending on cell species or number of cell nucleus to have a wave profile including a repetition of an attenuated wave profile portion and an amplified wave profile portion.

21. The light measurement method according to claim 19, wherein the intensity of the transmitted light varies over time depending on cell attribution and property expressed by number of cell nucleus and size of cell nucleus.

22. A light measurement method in which a irradiating light is irradiated to a cell in a liquid and a transmitted light transmitting the liquid and the cell is received to measure optical information of the cell, comprising:
irradiating the irradiating light to the cell from a light source portion;
irradiating the irradiating light from the light source portion to the liquid under a condition in which a relative position of the cell to the irradiating light varies at constant speed to receive the transmitted light by light receiving portion;
approximating wave profile of intensity of the transmitted light varied over time to one or plurality of standard template prepared in advance to be separated in layer; and
identifying property of the cell, wherein
a kind of the cell or cancer cell representing different property from same kind of cell is specified by wave profile varied over time, including a repetition of an attenuated wave profile portion and an amplified wave profile portion with the use of intensity of the transmitted light.

23. The light measurement method according to claim 22, wherein a cell of kind A, a cell of kind B, or a cell of kind B in a cell of kind C is specified, or abnormal cell in a cell of kind A is specified as cancer cell with use of the wave profile varied over time.

24. The light measurement method according to claim 22, wherein a specific cell including blood cell is specified according to the wave profile varied over time.

25. The light measurement method according to claim 18, wherein wavelength of the transmitted light is from 325 nm to 900 nm.

26. The light measurement method according to claim 25, wherein the irradiating light irradiated toward the cell from the light source portion expands from the light source portion toward the light receiving portion.

27. The light measurement method according to claim 25, wherein the light receiving portion comprises a CCD (charge-coupled device) camera, and in either state of that the cell flowing in a narrow flow passage or the cell is stationed in the liquid, the intensity of the receiving light signal and the two dimensional distribution state of the intensity of the receiving light signal can be measured by the stationing or varying of the relative position among the cell, the irradiating portion and the light receiving portion.

28. The light measurement method according to claim 22, wherein varied wave profiles of the intensity of the transmitted light to the cell in a parent population are divided into a plurality of groups, and the cell is distinguished from the parent population and evaluated with a frequency distribution of the respective groups.

29. The light measurement method according to claim 22, wherein wave profile is divided in layer into a plurality kinds from a measurement result of wave profile of the transmitted light obtained by a plurality of cells, and a kind of cell and state of cell is specified according to statistical information of each kind to all.

30. The light measurement method according to claim 22, wherein an amplification of the transmitted light is a variation of the intensity of the transmitted light over time measured by interference phenomenon of the transmitted light caused by attribution and property of the cell including size of the cell, and number and size of the cell nucleus.

31. The light measurement method according to claim 22, wherein an arbitrary sample is sorted from an identification result.

32. The light measurement method according to claim 31, wherein a specified cell is dispensed and selected.

33. The light measurement method according to claim 32, wherein selected cell is cultivated, or a prescribed reagent is added to the selected cell, and the variation over time of the selected cell is evaluated.

* * * * *

UNITED STATES PATENT AND TRADEMARK OFFICE
CERTIFICATE OF CORRECTION

PATENT NO. : 8,211,708 B2  
APPLICATION NO. : 12/610396  
DATED : July 3, 2012  
INVENTOR(S) : Ken Tsukii et al.

Page 1 of 1

It is certified that error appears in the above-identified patent and that said Letters Patent is hereby corrected as shown below:

On the title page, please insert the following item:

--Related U.S. Application Data  
(63) Continuation of application No. 12/403,701, filed on March 13, 2009, now abandoned.--

Signed and Sealed this  
Nineteenth Day of March, 2013

Teresa Stanek Rea  
*Acting Director of the United States Patent and Trademark Office*